United States Patent [19]
Frantz et al.

[11] Patent Number: 5,695,769
[45] Date of Patent: Dec. 9, 1997

[54] PASTEURELLA MULTOCIDA TOXOID VACCINES

[75] Inventors: Joseph C. Frantz; David S. Roberts; Leroy A. Swearingin, all of Lincoln; Richard J. Kemmy, Gretna, all of Nebr.

[73] Assignee: Pfizer Inc., New York, N.Y.

[21] Appl. No.: 244,052

[22] PCT Filed: Nov. 13, 1992

[86] PCT No.: PCT/US92/10008

§ 371 Date: Jul. 11, 1994

§ 102(e) Date: Jul. 11, 1994

[87] PCT Pub. No.: WO93/09809

PCT Pub. Date: May 27, 1993

Related U.S. Application Data

[63] Continuation of Ser. No. 792,490, Nov. 15, 1991, abandoned, which is a continuation-in-part of Ser. No. 537,454, Jun. 13, 1990, Pat. No. 5,536,496.

[51] Int. Cl.$^6$ ............... A61K 39/102; A61K 39/10; A61K 39/116; A61K 39/02
[52] U.S. Cl. .................. 424/255.1; 424/236.1; 424/253.1; 424/203.1; 424/93.3
[58] Field of Search ................. 424/203.1, 255.1, 424/253.1, 236.1, 93.3

[56] References Cited

PUBLICATIONS

Bescham Laboratories Atrobac 3 No. pp. 1–7, 1989.
Pejsak et al. J. Vet Meth. B. 37: 543–598, 1990.
Layton et al Avian Diseases 28:1086–1095, 1984.
Animal–Pharm 186 p. 22 Beecham's Lab's New Pig Vaccine Aug. 18, 1989.
Kohisch et al The Veterinary Record 124:57–61 1989.
Database Search: Animal Pharm, Showing veterinary biological licences issued in May 1989.
Daniel et al Proceedings American Association of Swine Practitioners, Mar. 1986, pp. 77–95.
J.C. Baars et al., 1986, Proc. Int'l. Pig Vet. Soc., 9th Cong., Challenge and field experiments with an experimental atrophic rhinitis vaccine, containing *Pasterella mutocida* DNT–toxoid and *Bordetella bronchiseptica*, p. 247.
K. Barfod et al., 1984, Nord. Vet.–Med. 36:337–345, Influence of vaccination of sows with *Bordetella–Pasteurella* vaccines on the occurrence of atrophic rhinitis among their offspring after experimental infection with *Bordetella bronchiseptica* and toxigenic *Pasteurella multocida*.
M.F. de Jong et al., 1986, Proc. Int'l. Pig Vet. Soc., 9th Cong., Neutralization–test against AR–toxin of *Pasteurella multocida* in pig herds after vaccination with Ar–vaccines.
M. F. de Jong et al., 1984, Proc. Int'l. Pig Vet. Soc., 8th Cong., Atrophic rhinitis in pigs induced by the intramuscular administering of "the Ar–toxin" containing bacteria–free broth culture filtrate, p. 161.
J. Descamps et al., 1986, Proc. Int'l. Pig Vet. Soc., 9th Cong., Vaccination study for protection against the dermonecrotic toxin of *Pasteurella multocida* type D.

N.T. Foged et al., 1989, Vet. Rec., 125:7–11, Protection against progressive atrophic rhinitis by vaccination with *Pasteurella multocida* toxin purified by monoclonal antibodies.
K.L. Heddleston et al., 1966, J. Immun., 96:124–133, Immunizing and toxic properties of particulate antigens from two immunogenic types of *Pasteurella multocida* of avian origin.
J.Y. Kim et al., 1986, Res. Rept., 28:77–93, Studies on immunogenicity of *Pasteurella multocida* isolated from swine in Korea (Abstract in English).
Y.S. Lu et al., 1987, Infect. Immun., 55:2967–2976, A potassium thiocyanate vaccine prepared from *Pasteurella multocida* 3:A protects rabbits against homologous challenge.
M. Matsumoto et al., 1977, Avian Dis., 21:382–393, A bacterin against fowl cholera in turkeys: protective quality of various preparations originated from broth cultures.
T.K.S. Mukkur, 1979, J. Gen. Microbiol., 113:37–43, Immunogenicity of a chaotropically extracted protective antigen(s) of *Pasteurella multocida* type A (bovine origin) against experimental Pasteurellosis in mice.
T. Nakai et al., 1984, Infect. Immun., 46:429–434, Purification of dermonecrotic toxin from a sonic extract of *Pasteurella multocida* S72 serotype D.
J. M. Park et al., 1988, Res. Rep. Rural Dev. Adm., 30:28–36, Studies on the combined vaccine of swine bacterial diseases containing *Pasteurella–multocida Bordetella–bronchiseptica Erysipelothrix–rhusiopathiae Escherichia–coli* (Abstract only).
K. B. Pedersen et al., 1981, Nord. Vet. Med., 33:513–522, The aetiological significance of *Bordetella bronchiseptica* and *Pasteurella multocida* in atrophic rhinitis of swine.
K. B. Pedersen et al., 1982, Nord. Vet. Med., 34:293–302, Effect on the incidence of atrophic rhinitis of vaccination of sows with a vaccine containing *Pasteurella multocida* toxin.
P. A. Rebers et al., 1984, Carb Res., 133:83–94, The effect of formalin–killing of *Pasteurella multocida* on the antigenicity and extractability of its lipopolysaccharide.
J. M. Rutter, 1983, Res. Vet. Science, 34:287–295, Virulence of Pasteurella multocida in atrophic rhinitis of gnotobiotic pigs infected with *Bordetella bronchiseptica*.
D. Schimmel, 1990, Berl. Munch. Tier. Woch., 103:410–411, Further development of *Pasteurella multocida* vaccines for pigs (Abstract only).
R. Singh et al., 1988, Singapore J. Primary Industries, 16:24–33, Efficacy of an inactivated broth–grown *Pasteurella multocida* bacterin in ducklings (Abstracts only).

Primary Examiner—Hazel F. Sidberry
Attorney, Agent, or Firm—Peter C. Richardson; Paul H. Ginsburg; Alan L. Koller

[57] ABSTRACT

This invention provides vaccine compositions, methods of producing same and methods for protecting porcine animals against disease associated with infection by toxigenic *Pasteurella multocida*. The vaccines of this invention contain effective amounts of a *P. multocida* bacterin with a cell-bound toxoid and, optionally, a *P. multocida* free toxoid.

14 Claims, No Drawings

PASTEURELLA MULTOCIDA TOXOID VACCINES

CROSS-REFERENCE TO RELATED APPLICATIONS

This application is the United States national stage of International Application No. PCT/US92/10008, filed Nov. 13, 1992, which is a continuation of U.S. application No. 07/792,490, filed Nov. 15, 1991, now abandoned, which is a continuation-in-part of application no. 07/537,454, filed Jun. 13, 1990, now U.S. Pat. No. 5,536,496.

FIELD OF THE INVENTION

This invention is generally in the field of veterinary vaccines, vaccine compositions, and methods of producing same. More particularly, this invention relates to vaccine compositions and methods for protecting animals against diseases associated with infection by toxigenic strains of *Pasteurella multocida*.

BACKGROUND OF THE INVENTION

*Pasteurella multocida* has been associated with disease in many species of animals, including man, bovine, ovine and porcine animals. It typically affects the nasopharyngeal regions and lungs of infected animals. For example, in a mixed infection with *Bordetella bronchiseptica* toxigenic strains of *P. multocida*, capsular type A or D, cause atrophic rhinitis in swine. Atrophic rhinitis (AR) results in atrophy of the nasal turbinates and deformities of the snouts and faces of pigs.

The pathogenicity of *P. multocida* is due in large part to the production of a potent necrotizing toxin, also called dermonecrotizing toxin (DNT), which will be referred to hereinafter as "the toxin". The toxin has been characterized as a heat-labile protein with a molecular weight of approximately 140,000 to 160,000.

*P. multocida* is distinguishable from other species of pasteurella on the basis of its growth characteristics, as follows: hemolysis: negative (90%); growth on MacConkey's agar: negative; indole production: positive; urease production: negative; and mannitol metabolism: positive. See, Zinsser, *Microbiology*, edit. by Joklik et al., Appleton-Century-Crofts, New York, 1980, pages 791–793, which is incorporated herein by reference.

Currently available vaccines for protecting animals from diseases associated with infection by *P. multocida*, include inactivated toxigenic *P. multocida* cells, inactivated preparations of partly purified *P. multocida* toxin and combinations of *P. multocida* cell-free preparations with other inactivated *P. multocida* strains or *B. bronchiseptica* strains. [See, e.g., M. Kobisch et al, *Vet. Record*, 124: 57–61 (1989); and N. T. Foged et al, *Vet. Record*, 125: 7–11 (1989)]. These vaccine preparations, however, are not fully protective against disease because they fail to elicit effective amounts of the antibody that neutralizes the toxin, known as "antitoxin".

There remains a need in the art of veterinary practice for effective vaccines against infection of animals by toxigenic *P. multocida*.

SUMMARY OF THE INVENTION

The present invention provides novel vaccine compositions and components which protect animals against disease associated with infection by toxigenic *Pasteurella multocida*. These vaccine compositions are characterized by the ability to elicit significant quantities of circulating antitoxin.

In a first aspect, the invention provides a novel vaccine composition containing a whole *Pasteurella multocida* killed cell (bacterin) with cell-bound toxoid. This composition can induce in a previously unvaccinated animal a superior antitoxin response compared to the free, soluble toxoid. This composition is associated with a carrier suitable for internal administration, preferably aluminum hydroxide gel.

In another aspect, the invention provides a novel vaccine composition comprising (1) a whole *Pasteurella multocida* bacterin with cell-bound toxoid which, upon internal administration to an animal, induces an antitoxin response, and (2) a free, soluble toxoid of *P. multocida*. This vaccine composition produces an unexpected synergistic antitoxin response, much greater than the sum of the separate effects of the two components. A carrier is desirably associated with this composition.

The soluble cell-free toxoid of *P. multocida* is produced by a method that employs subjection of the toxin to varying pH and temperature, which method is also a novel aspect of the present invention. The term "toxoid" describes a preparation of the toxin that has been inactivated ("toxoided") by a process that abolishes its toxicity without destroying its ability to induce the production of the specific neutralizing antitoxin.

In a further aspect the above vaccine compositions may be varied by combination with an immunogenic amount of one or more additional antigens. Preferred antigens include, a *B. bronchiseptica* bacterin, an *Erysipelothrix rhusiopathiae* bacterin, a *Mycoplasma hyopneumoniae* extract vaccine. However, other conventional vaccine components may also be added to the vaccine compositions of this invention.

The vaccine compositions of this invention are administered internally in dosage units. In one embodiment, a vaccine dose comprises 0.5 to 3 mL of a sterile suspension of an immunogenic amount of a *P. multocida* bacterin with cell-bound toxoid which, upon internal administration to an animal, induces an antitoxin response. Another embodiment is a dosage unit comprising 0.5 to 3 mL of a sterile mixture of the *P. multocida* cell-bound and free toxoids. Still another embodiment is a dosage unit comprising 0.5 to 3 mL of a sterile mixture of immunogenic amounts of the free and cell-bound toxoids and one or more additional antigenic components.

In yet another aspect, the invention provides a method of preparing an Erysipelothrix vaccine component that is free of serum and virtually free of bacterial cells.

Yet a further aspect of this invention is a method for vaccinating an animal against atrophic rhinitis, that comprises internally administering to the animal an effective amount of one or more of the *P. multocida* toxoid vaccine compositions described above.

Other aspects and advantages of the present invention are described further in the following detailed description of preferred embodiments thereof.

DETAILED DESCRIPTION OF THE INVENTION

The present invention provides vaccine compositions useful in the prophylaxis of diseases resulting from infections with toxigenic *P. multocida* and other pathogenic organisms including *Erysipelothrix rhusiopathiae*, *Bordetella bronchiseptica*, and *M. hyopeneumonia*. Such diseases include atrophic rhinitis (AR), pleuritic and pneumonic pasteurellosis, erysipelas, and pneumonia.

One embodiment of this invention provides a whole bacterin-toxoid of *P. multocida* which contains toxoid confined and stabilized within the bacterial cell. This cell-bound toxoid is prepared either by known methods as described in Example 1, or preferably by the procedure for preparing Gram-negative bacterial fluids for use in vaccines which is described below. An inactivating agent is added to a *P. multocida* culture that is still growing exponentially and that has not yet begun to release the toxin into the growth medium. The toxoid is thereby confined within the bacterial cell. The dead bacterial cells, i.e., bacterins, with the toxoid sequestered safely within, are ideal antigenic particles for presentation to those host cells that mediate the immunizing process. This is especially important for animals that have not previously been exposed to the toxin or the toxoid and that totally lack antitoxin. The *P. multocida* cell-bound toxoid of this invention is remarkably stable. Loss of antigenic potency was undetectable after storage at 4° C. for more than two years.

For purposes of this invention, the cell-bound toxoids described above can be derived from any strain of *P. multocida* which elaborates the toxin. Several such strains are available, e.g., from the American Type Culture Collection, Rockville, Maryland or from a variety of veterinary colleges or laboratories. Examples below refer to *P. multocida*, Type D, strain 8 and strain 4677.

Presently, *P. multocida*, type D, strain 4677 is preferred for the preparation of the cell-bound toxoid. This strain is particularly advantageous because, when equivalent numbers of cells of each strain are use, strain 4677 is capable of producing twice as much toxin as strain 8 which was previously the best, known, toxin producer. This capacity of strain 4677 to produce twice the amount of toxin is advantageous because only half the amount of strain 4677 culture, i.e. half the number of cells, is required to produce the same amount of toxin as is produced in a strain S culture. Additionally, because space in a combination vaccine is limited, e.g., a 2 mL dose, the fact that strain 4677 fluids occupies half the space occupied by strain 8 fluids provides a significant advantage over prior art vaccines. Thus, *P. multocida* strain 4677 confers a formulational benefit not available with previously used strains.

Suitable culture media for use in growing the *P. multocida* cultures may be selected by one of skill in the art, but preferably include, without limitation, the medium described by Herriott et al, "Defined Medium for Growth of *Hemophilus Influenzae*", *J. Bact.*, 101: 513–516 (1970).

The above described, novel, whole cell-bound toxoid may be employed separately in a vaccine composition for induction of an antitoxin response that will prevent the pathological changes characteristic of atrophic rhinitis. In the vaccine composition, an immunogenic amount of the cell-bound toxoid is desirably mixed with suitable conventional vaccine adjuvants and physiologic vehicles, for injection into mammals, especially swine.

A more preferred vaccine composition is provided by a synergistic combination of a *P. multocida* free toxoid (described below) and the cell-bound toxoid (described above). Such a combination vaccine is prepared by mixing an immunogenic amount of free toxoid and an immunogenic amount of cell-bound toxoid with suitable adjuvants and physiologic vehicles for injection into mammals. Preferred adjuvants include aluminum hydroxide gel.

As described above, the free, soluble *P. multocida* toxoid is useful in synergistic combination with the *P. multocida* cell-bound toxoid. The free, soluble toxoid is the subject of co-pending U.S. patent application No. 071537,454, now U.S. Pat. No. 5,536,496 incorporated by reference herein.

Although any toxigenic *P. multocida* strain may be used for the preparation of the soluble toxoid, the strain used below in the examples is *P. multocida*, type D, strain 8, which is available, upon request, from the University of Illinois. The soluble toxoid is prepared generally by extracting toxin from the bacterial cells and causing a partial denaturation by incubating the cell-free toxin for about 12 to 24 hours at a pH greater than 9, at an incubation temperature of between about 12° C. and 19° C.

More specifically, the free toxoid is prepared as follows. A selected toxigenic *P. multocida* strain is grown in a suitable culture medium. At the end of growth cycle, the toxin is liberated from the cells by conventional physical or chemical means e.g., french press or sonic disruption, and cellular debris is removed by centrifugation and filtration. It has been determined that for large-scale production the following pH cycling desirably accompanies incubation. The cell-free extracted toxin is then incubated, cycling between a pH of about 10.5 and about 6.80 three times over a period of at least 21 hours. A similar procedure described in the above-referenced patent application was used for laboratory scale production. This process results in complete detoxification of the toxin, providing a toxoid soluble in aqueous solutions (e.g. phosphate buffered saline, tris buffered saline).

The soluble *P. multocida* toxoid preparation is both antigenic and immunogenic. Specifically, the soluble toxoid can elicit antibodies that can bind to the toxin, and neutralize its toxicity. Further, the soluble toxoid of this invention is characteristically stable 4° C. for at least 24 months, which is a highly advantageous commercial characteristic, indicating that this vaccine may be stored for later use.

In vaccination experiments with animals, as reported below in Example 11, free and cell-bound toxoids have been found to act synergistically in a single vaccine preparation, i.e., the vaccine produces in the vaccinated animal a surprisingly greater effect than that expected by simply adding the effects of each toxoid component administered separately. This combination vaccine stimulates a remarkable production of antitoxin in tested animals. This combined effect may also be generated by sequentially administering the cell-bound toxoid vaccine, followed by an injection of the soluble toxoid vaccine.

While not wishing to be bound by theory, it is presently believed that the cell-bound toxoid vaccine primes the animals, particularly immunologically naive animals incapable of responding to soluble toxoid. A second dose of the cell-bound toxoid induces a moderate secondary response. Once primed by the toxoid-rich cells, however, the animals are very responsive to the soluble free toxoid. Just as the cell-bound toxoid is a superior priming agent, the soluble toxoid has been observed to be a superior booster.

Still other preferred vaccine compositions of this invention result from combining the cell-bound toxoid of this invention, with or without the free toxoid, with other vaccinal agents. An illustrative example is a vaccine composition formed by the combination of a whole *B. bronchiseptica* bacterin with the *P. multocida* cell-bound toxoid. Alternatively, the above composition further contains *P. multocida* free toxoid. This free toxoid may be derived from a capsular type of *P. multocida* different from the type used to make the cell-bound toxoid. Further, a vaccine composition of this invention may also include an *E. rhusiopathiae* component. Thus, in another aspect, the present invention provides a method of preparing an erysipelothrix vaccine component.

Other possible vaccinal agents which may be combined with the vaccine components of this invention include, without limitation, *Escherichia coli*, pneumonic *P. multocida*, *Streptococcus suis*, *Actinobacillus pleuropneumoniae*, *Clostridium perfringens* types C and D toxoids, Pseudorabies Virus Vaccine (modified live virus and/or killed virus), Rotavirus Vaccine (modified live virus), Coronavirus Vaccine (modified live virus).

In one preferred embodiment, *Mycoplasma hyopneumoniae* is also included in the vaccine composition of the present invention in combination with at least the *P. multocida* cell-bound toxoid. *M. hyopneumoniae* strains useful in preparing a vaccine of the present invention can be isolated from swine infected with wild-type or other known strains causing mycoplasmal pneumonia in swine. Other known strains of *M. hyopneumoniae*, both virulent and avirulent, may be useful in the compositions of this invention. Useful strains may be obtained from commercial or academic sources. A particularly preferred strain of *M. hyopneumoniae* for use in embodiments of this invention is identified as strain P-5722-3, ATCC #55052, deposited on May 30, 1990 pursuant to the accessibility rules required by the U.S. Patent and Trademark Office. Methods of preparing *M. hyopneumiae* vaccine components are described in Example 10 below. More detailed information regarding these vaccines is presented in copending U.S. patent application No. 07/634,237, which is incorporated by reference herein.

Vaccines of the invention may be prepared as pharmaceutical compositions containing an effective immunogenic amount of the cell-bound toxoid as the active ingredient in a nontoxic and sterile pharmaceutically acceptable carrier. A preferred embodiment of the vaccine of the invention is composed of an aqueous suspension or solution containing the cell-bound toxoid, preferably buffered at a pH of approximately 6.5, in a form ready for injection.

Additionally, the cell-bound toxoid, whether administered alone or in combination with the free toxoid, can be admixed or adsorbed with a conventional adjuvants and added to the vaccine composition of the invention. The adjuvant is used as a non-specific agent to enhance the specific antitoxin response. Such adjuvants include, among others, AMPHI-GEN® adjuvant [Hydronics, Inc.] or other dispersed oils, aluminum hydroxide, muramyl dipeptide, and saponins, such as Quil A.

In yet another exemplary alternative, the cell-bound toxoid, with or without the free toxoid, can be administered with another antigenic preparation, such as *B. bronchiseptica* bacterin, *E. rhusiopathiae* bacterin, or *M. hyopneumoniae*, which may be prepared by known techniques or, preferably, by the techniques described herein.

One of the preferred techniques for preparing bacterial components of this invention is a novel method of preparing Gram negative bacteria for inclusion in a vaccine formulation. This method can be applied to, and may utilize, antigenic concentrates of any kind including, but not limited to, whole-cell suspensions and cell-free extracts of Gram-negative bacteria. This new method is the subject of a co-owned, concurrently filed patent application and is described below.

According to this method, selected Gram-negative bacteria, e.g., the Gram negative bacteria described herein, such as Pasteurella, are grown under conventional conditions in any suitable culture medium, conventional or otherwise. Suitable media may be selected by one of skill in the art with resort to conventional knowledge. Preferably, the temperature of the bacterial culture during growth ranges between 35° and 38° C.

While growth is still transitional, or preferably exponential, an inactivating agent is added if whole bacteria are to be used in the resulting vaccine component. Preferably, the inactivating agent is a fixative capable of binding the cellular structure and preventing disintegration of the cell wall. One fixative is formalin (formaldehyde solution USP), which is usually used at a concentration of about 0.3% v/v to about 1.0% v/v. Another fixative, which is useful when synthetic media are used, is glutaraldehyde. For example, for between about 0.5 and 1% v/v of a 25% aqueous glutaraldehyde solution may be used. Other suitable inactivating agents, such as betapropiolactone, may also prove useful, and appropriate concentrations can be readily determined by one of skill in the art.

When the inactivating agent is added, aeration and automatic pH controls are switched off. Optionally, the pH may be adjusted to optimize inactivation. Stirring or agitation is decreased to the minimum that will give fast, efficient mixing. Although inactivation conditions are dependent upon the particular bacterial species and can be readily determined by one of skill in the art, inactivation is typically carried out at between about 28° to 38° C.

Alternatively, if cell extracts are to be prepared for use in a resulting vaccine composition, inactivation may not be required. In such a case, the culture may be cooled to arrest growth, usually to a temperature of less than 20° C. Extraction may be performed prior to, or following, the concentration steps described below.

The bacteria are concentrated by centrifuging or filtering the cells to a dense, concentrated aqueous suspension or extracted. Centrifugation preferably occurs at a force of about 10,000 g. Appropriate higher or lower forces may be used if the rate of flow of culture fluid through the centrifuge is adjusted to ensure recovery of nearly 100% of the cells, depending upon the bacterial species. The appropriate rate of flow can also be determined by one of skill in the art by monitoring the optical density of the effluent supernatant fluid, which is discarded. Other concentration methods may be used in place of centrifugation, such as ultrafiltration. The methods as well as conditions and apparatus necessary to ensure recovery of approximately all of the cells is within the skill of the art. Regardless of the concentration method selected, the cells are collected in as small a volume of culture effluent as can consistently be attained from batch to batch. Preferably the cell concentrate contains between about $10^9$ to about $10^{11}$ cells/ml of culture fluid. This same concentration may be used prior to extraction for preparation of a concentrated cell extract.

The resulting cell concentrate is diluted with a small amount of water, saline or buffer, to a selected standard concentration that is independently established for the concentration method. The establishment of the standard depends on the particular bacterium and may be selected by one of skill in the art provided with the above teachings.

The aqueous concentrated suspension or extract is then adsorbed with an appropriate mineral carrier. The carrier useful in this invention may include an aluminum hydroxide, aluminum phosphate, an alum, usually potash alum (aluminum potassium sulfate), or calcium phosphate, which compounds are capable of tightly binding endotoxin. Presently, the preferred carrier is an aluminum hydroxide gel of high binding power. Such aluminum hydroxide gels are commercially available, for example, REHYDRAGEL™ low viscosity gel or REHYDRAGEL™ HPA (high power) gel [Reheis Chemical Co., Berkeley Heights, N.J.].

The carrier is preferably added to the pre-diluted suspension of bacterial cells or cell extracts at a concentration that is usually between about 15 and 60% v/v. This concentration is determined by titration to produce optimal avidity in the carrier and, hence, optimal binding of both endotoxin and immunogenic bacterial antigens. The titration end-point is a free endotoxin concentration of between about 2 and about 50 ng/ml. Titration techniques are readily known to one of skill in the art.

When using the REHYDRAGEL™ carrier, the absorption is performed at room temperature (approximately 20°–25° C.), preferably at a pH of about 6.5, with stirring for about 1 hour. One of skill in the could modify these conditions while using the process of the invention. For example, the absorption could be performed at a lower temperature, e.g. 4° C., but the time for mixing would have to be extended. Similarly, absorption could be performed at higher temperatures, e.g. 37° C., with a shorter mixing time depending upon the stability of the antigens at this temperature.

After adsorption is performed, the resulting adsorbed suspension or extract is diluted for use in vaccine compositions. Depending on the selected standard concentration of the suspension or extraction, the dilution may be between about 5 to about 50-fold produce suitable vaccine compositions.

This above-referenced method thus involves firmly binds endotoxin present in the Gram-negative bacterial concentrate with the selected carrier. The binding of the endotoxin in the concentrated cell or extract makes the resulting fluids, after dilution, safe for vaccine use in animals. This binding eliminates the vaccine's systemic reactivity in vaccinated animals the same time, the low concentration of mineral carrier in the finished vaccine avoids the adverse injection site reactions associated with the use of conventional concentrations, e.g., greater than 10%.

While not wishing to be bound by the theory of the mechanism by which this method works, the inventors believe that a Gram-negative bacterial cell suspension or extract-containing product prepared by this method is systemically safe because the release of endotoxin in the injection site is greatly delayed. It is the rapid entry of free endotoxin into the system that causes shock. When the avidity of the carrier gel is modulated or optimized according to the method of the invention, some antigens are not bound, e.g. bacterial cells. Others, e.g., important protein antigens such as endotoxin, are bound more loosely (or less tightly) than by fully avid gels loose enough to permit ready uptake by macrophages and, hence, the retention of good immunogenicity.

The resulting bacterial fluids, treated and diluted as described above, may then be used alone as vaccine preparations or combined with other vaccine components. Preferably, the resulting vaccine compositions containing Gram-negative cells or cellular extracts, prepared according to this method, also contain between approximately 0.1 and 10% v/v of the aluminum carrier compound, and more preferably, between about 0.5 and 5% v/v.

A vaccinal fluid prepared according to this method also significantly contains a free endotoxin concentration of between about 2 and 250 nanograms per mL, preferably between 2 and 50 ng per mL, after adsorption and before dilution. The pH of a vaccine composition prepared according to this method should finally be adjusted to about 6.5±0.5, but preferably ±0.2. The quantification of the free-endotoxin concentration in the vaccinal fluids may preferably be assayed by the LAL method [Levin et al, *Bull. Johns Hopkins Hosp.*, 115: 265 (1964) and Levine et al, *Thromb. Diath. Haemorrh.*, 19: 186 (1968)]. Other methods may also be used to assay the endotoxin levels.

According to the present invention, preferably, a pharmaceutical preparation provides a unit dose of between 0.5 and 3 mLs, and more preferably approximately 2 mL, of a sterile preparation of an immunogenic amount of the active ingredients, whether the active ingredient is the cell-bound toxoid only, a combination of the cell-bound toxoid and the free toxoid, or one of these two formulations further containing additional active agents.

For purposes of this invention, an immunogenic amount of *P. multocida* cell-bound toxoid is measured in units called opacity or absorbency units (O.U. or A.U., respectively). These units refer to the optical density (O.D.) of 1 mL as measured at a wavelength of 625 nm in a Spectronic 20 spectrophotometer. An immunogenic amount of the cell-bound toxoid is preferably between 1 and 5; more preferably, the free toxoid is administered in an amount of approximately 2 A.U.

For purposes of this invention, an immunogenic amount of free toxoid, when administered in combination with the *P. multocida* cell-bound toxoid of the invention, is between about 6.5 and 8.1 micrograms per dose. In contrast, when the free toxoid is administered to an immunologically naive animal alone, it induces no antitoxin. This demonstrates the interaction between the free toxoid and the cell-bound toxoid.

These immunogenic amounts of the free toxoid may also be defined in terms of relative toxoid units ("RU"). Desirably, a free toxoid/cell-bound toxoid vaccine composition contains between, 80 and 1000 RU, and more desirably, between 80 and 150 RU per dose of free toxoid. The value of RU was determined empirically based on an estimate of the amount of toxoid which, when inoculated into mice, would elicit an antitoxin response that protected half the mice against the lethal effects of intraperitoneal inoculation of approximately 30 $LD_{50}$ of purified toxin. Thus one RU is approximately equal to one mouse $PD_{50}$.

The *P. multocida* cell-bound toxoid of the invention, whether administered with or without the *P. multocida* free toxoid, may contain additional active ingredients. Currently, the most preferred additional active ingredients are a *B. bronchiseptica* component, an *E. rhusiopathiae* component, and a *M. hyopneumoniae* component.

For purposes of this invention, when *E. rhusiopathiae* s prepared as described in Example 7 below, the minimum immunogenic amount of this component is 3.40.U. Opacity units are as defined above except that the OD readings were taken at a wavelength of 650 nm.

For purposes of this invention, an immunogenic amount of *B. bronchiseptica*, prepared as described in Example 8 below, is measured in units termed nephelometric units. The required immunogenic amount of this component is dependent upon the method used to obtain it in an inactivated, yet immunogenic form. For example, if the *B. bronchiseptica* is inactivated by betapropiolactone (BPL), at least 1500 nephelometric units are required for immunogenicity. If it is inactivated by the glutaraldehyde method at least 3000 nephelometric units are required. If it is inactivated by formaldehyde, at least 4500 nephelometric units are required. One of skill in the art could determine other, appropriate immunogenic amounts if other inactivation techniques are used. This component is included in the vaccine composition of the invention to protect against atrophic rhinitis.

For purposes of this invention, an immunogenic amount of *M. hyopneumoniae*, prepared as described below in Example 10, is measured in units termed color changing units (CCU) [Rodwell and Whitcomb in *Meth. n Mycoplasmology*, Vol. 1, p. 188 et seq., Academic Press, N.Y. (1983)]. Preferably, a vaccine composition of this invention contains approximately $5 \times 10^9$ CCU. However, it is contemplated that conditions can be optimized so that this amount can be reduced to between approximately $5 \times 10^8$.

A desirable dose regimen involves administration of two doses of desired vaccine composition, where the antigenic content of each fraction is desirably as stated above. The mode of administration of the vaccines of the invention may be any suitable route which delivers the vaccine to the host. However, the vaccine is preferably administered subcutaneously or by intramuscular injection. Other modes of administration may also be employed, where desired, such as intradermally or intravenously.

Present investigations with swine employ intramuscular injection of two doses of vaccine at an interval of two weeks. These studies have shown that, for each of the above described vaccine compositions, a primary immunization of newborn animals is desirably initiated at about one week of age with a booster dose at weaning age. For primary immunization of pregnant dams, two doses are recommended with the last dose administered about two weeks before farrowing. A booster dose is recommended prior to each subsequent farrowing. Semi-annual revaccination is recommended for boars.

The specific mechanism of protection against *P. multocida* induced by the vaccine compositions of the present invention is the induction of toxin-neutralizing antibody (antitoxin) in vaccinated animals, as indicated by the in vivo animal tests described below.

The examples which follow illustrate preferred methods for preparing the cell-bound toxoid of the invention and for preparing and testing a variety of vaccines containing this novel component. These examples are illustrative only and do not limit the scope of the present invention.

EXAMPLE 1

PREPARING *P. MULTOCIDA* CELL-BOUND TOXOID

An embodiment of this composition includes a cell-bound toxoid of *P. multocida* in which the toxoid has been stabilized within the bacterial cell.

*P. multocida* Type D, strain 4677, was isolated from an infected pig at the Illinois Animal Disease Laboratory, Galesburg, Ill. [Dr. Douglas Hoefling]. The strain was subcultured twice on agar. The growth from the second subculture was suspended in a sterile solution of 10% NZ Amine, 1% gelatin, and 10% glycerol. Ampules of the suspension were frozen in liquid nitrogen. This master seed is stored at SmithKline Beecham Animal Health [White Hall, Ill.].

Seed and production cultures of *P. multocida*, Type D, strain 4677, are grown in the following medium: 30 g Tryptic Soy Broth without dextrose [Difco] and deionized water to 1 liter, pH 7.5 for seed cultures or 7.0 for production cultures. The culture medium is sterilized by autoclaving at 121° C. for at least 20 minutes. After autoclaving, 50 mL of filter-sterilized yeast extract solution, 10% w/v, and 4 mL autoclaved dextrose solution, 50% w/v, are added. During incubation, more dextrose solution may be added as needed.

An ampule of working seed (subcultured from the master seed which is obtained as described above) is thawed, and its contents transferred to a container of seed medium, described above. The seed culture is incubated at 37° C. for 12 to 24 hours, with agitation. If the culture is satisfactory, as determined by Gram staining, it is used to inoculate the production culture. Alternatively, it may be used to inoculate a second seed culture. Inocula are 2 to 10% of the culture volume. Production cultures are incubated for 2 to 6 hours at 37° C. Dissolved oxygen is maintained at approximately 35% of saturation. The temperature is maintained at 37° C, and the pH at 7 by the addition of 10N NaOH solution as needed. Growth is monitored by periodic optical density (OD) readings at 625 nm.

Towards the end of exponential growth (when the $OD_{625}$ reaches approximately 2, aeration is discontinued and formaldehyde solution is added to a final concentration of 0.5% v/v. Inactivation is continued for 4 days at 37° C., with gentle or intermittent agitation. Pure cultures, as determined by Gram staining, having an OD of 2±0.5 and an L+ value of at least 6 units per mL are considered satisfactory for use in production. An L+ unit of toxin is equivalent to one unit of standard antitoxin [Roberts and Swearingin, *Am. J. Vet. Res.*, 49: 2168 (1988)] as shown by toxin-antitoxin titration in mice.

A sample is withdrawn to test whether inactivation is complete by administering the sample to guinea pigs. Guinea pigs should be alive and healthy at 7 days after subcutaneous injection with 4 mL volumes of the culture. At this point the toxin within the cells is completely converted to toxoid, which is safe, very stable and capable of inducing the production of neutralizing antitoxins upon injection into animals.

At the end of the inactivation period, the culture is cooled and then transferred aseptically into a holding vessel. The culture is separated aseptically into cellular and fluid fractions by passage through a sterile continuous-flow centrifuge. Both fractions are collected in sterile containers for further processing. Depending upon the OD at inactivation, the cellular fraction is diluted to a calculated OD of 12.5. This is done with a portion of the fluid fraction and a volume of sterile saline (0.85% NaCl) such that the final fluid fraction contains bacterial cells suspended in a liquid containing 40% culture fluid by volume, or 1% w/v peptone plus yeast extract.

After inactivation and concentration of the culture are complete, sterile aluminum hydroxide gel is added to a final concentration of 25% v/v. The free-formaldehyde content of the fluid is assayed, and decreased to 0.2% or less with sodium bisulfite. Thimerosal-EDTA solution (or another suitable preservative) is added as a preservative to a final thimerosal concentration of 0.01% v/v. The pH is checked and, if necessary, adjusted to 6.5±0.2.

This product is standardized to contain 1.875 absorbancy units calculated from the OD at inactivation. This standardized amount may be obtained in an 0–2 mL dose which may be internally administered alone, or in combination with other vaccinal components. Such a combination vaccine will usually have a total dosage amount of 2 mL.

EXAMPLE 2

PREPARING *P. MULTOCIDA* CELL-BOUND TOXOID

The cell-bound toxoid of this invention may also be prepared from *P. multocida* toxigenic strains other than strain 4677, described in Example 1 above.

For example, *P. multocida*, type D, strain 8 can be used to prepare cell-bound toxoid by the method described above. However, some minor changes must be made to accommodate the lower toxoid production capacity of strain 8 as compared with that of strain 4677.

A culture of *P. multocida*, type D, strain 8, is grown in the following medium: Tryptic Soy Broth without Dextrose (Difco) 30 g; Yeast extract (Difco) 5 g; Dextrose 4 g; Deionized water to 1 liter; pH of approximately 7; sterilized by autoclaving at 121° C. The culture is then grown, inactivated, concentrated (and dispensed in sufficient supernatant fluid to make a suspension with an OD of 4.2 (optical density at 625 nm, as determined in a Spectronic 20 spectrophotometer) and adjuvanted essentially as described above.

This product is standardized to contain 3.75 absorbancy units calculated from the OD at inactivation. This standarized amount can be administered alone, or in combination with other vaccinal components. Typically, such a combination vaccine will have a dose of approximately 2 mL.

EXAMPLE 3

PREPARING *PASTEURELLA MULTOCIDA* FREE TOXOID

A. Culturing the P. multocida

*P. multocida* type D (strain 8) [Dr. Ross Cowart, University of Illinois, Urbana, Ill.] is subcultured in the modified chemically defined synthetic medium described by Herriott et al, *J. Bact.* 101: 513–516 (1970) for one day. The pH of the assembled medium is adjusted to 7.3±0.2 with sterile NaOH. Cells from this culture are transferred to fresh synthetic medium and this culture, when grown, is combined with a cryopreservative and stored at −70° C. Production cultures are grown to harvest during incubation at approximately 36°±1° C. for between 3 and 24 hours following inoculation. The dissolved oxygen content of the culture is maintained by aeration with sterile air and by agitation. Sterile antifoam solution is used to control foam. The pH of the culture is maintained at 7.3±0.2.

At the end of the growth cycle, *P. multocida* cultures are examined and cell density is determined by absorbance at 650 nm. Agitation is then decreased, and aeration and pH control are discontinued.

The toxin content of the lysate is measured by mouse lethality ($LD_{50}$) and by the Enzyme-linked Immunosorbent Assay (ELISA) described below in Example 6.

B. Pre-detoxification treatment

Following growth of the organism, sterile merthiolate is added to the culture in an amount less than or equal to 0.01 percent weight per volume. Culture fluids may be aseptically transferred through closed connections to a sterile closed container. The container is connected through closed fittings to an apparatus used to physically lyse cells and release cellular contents, e.g., a "GAULIN" model 15M laboratory homogenizer.

Bacterial cells in the culture fluid are lysed by continuous passage through the pressure chamber of the homogenizer. This subjects the cells to an immediate pressure drop from between an initial pressure of about 2000 to about 5000 psi and ambient pressure of 15 psi. The lysed cells are aseptically deposited into another closed container.

The lysate is clarified by sequential steps of centrifugation and/or microporous filtration. Clarified solutions may be concentrated before or after filter sterilization. Ethylenediaminetetraacetic acid (EDTA), in an amount up to a final concentration of 5 mM, and glycerol, in an amount up to a final concentration of 1.0% (vol/vol), are added before concentrating and filter-sterilizing, to prevent aggregation of the concentrated proteins.

C. Detoxification

Sterile 5N NaOH is slowly and aseptically added to sterile toxin to increase the pH to approximately 10.55±0.10 pH units. At this pH, the detoxification occurs as the mixture is allowed to stir slowly at approximately 15°±1° C. for at least 7 hours. Sterile 5N HCl is then slowly and aseptically added to adjust the pH to 6.80±0.20 pH units. The pH is held at this lower level just long enough to take an aliquot. Residual toxicity of each aliquot is measured and expressed in mouse $LD_{50}$'s per mL.

The mixture is then adjusted back up to a pH of approximately 10.55±0.10 pH units as described above and held for 7 hours. At the end of this time, the mixture is again adjusted down to a pH of about 6.80±0.20 pH units long enough for an aliquot to be removed. The mixture is then cycled through these steps once again.

A preparation with an initial value of nearly 10,000 $LD_{50}$'s per mL is usually detoxified 21 hours after this pH cylcing process is begun, without appreciable decrease in assayable antigen content. The toxoid is then stored at 2° to 7° C. until combined with other components and assembled into vaccine compositions.

EXAMPLE 4

VACCINE FORMULATION CONTAINING FREE TOXOID

An illustrative free toxoid vaccine formulation was made by preparing the soluble free toxoid as described above in Example 3.

To make a vaccine, the toxoid is diluted in sterile buffered saline at a neutral pH. Sterile aluminum hydroxide gel is used as adjuvant and added at a level sufficient to adsorb toxoid, generally 12%±1% (vol/vol). The vaccine compositions are prepared by thoroughly mixing, then dispensing the indicated amount of toxoid and aluminum hydroxide gel into a 500 ml beaker. Sterile saline is then added. This mixture is stirred and stored at 4° C. Dosage amounts of 2 ml/dose are desirable, which provides about 450 relative dosage units per dose. Table I illustrates the formulation of two free-toxoid vaccines.

TABLE I

| Experimental Lot | Component | Total Volume |
|---|---|---|
| A | Toxoid Concentrate | 150.0 ml |
|   | Aluminum Hydroxide Gel | 36.0 ml |
|   | Sterile Saline | 114.0 ml |
|   | Total | 300.0 ml |
| B | Toxoid Concentrate | 235.0 ml |
|   | Aluminim Hydroxide Gel | 41.0 ml |
|   | Sterile Saline | 304.0 ml |
|   | Total | 580.0 ml |

These free toxoid vaccine formulations are useful as an aid in prevention of atrophic rhinitis in swine caused by *P. multocida* infections. An exemplary test of the free toxoid vaccine is performed by injecting the formulations into swine (pigs and dams) as described below.

EXAMPLE 5

EXPERIMENTS WITH FREE TOXOID VACCINE

Using the formulations of Example 4, vaccines were administered intramuscularly to pigs and dams selected at random according to the following protocols. In each test after vaccination the animals were challenged with purified toxin at a dose known to consistently induce clinical signs of atrophic rhinitis in pigs. Toxicity of DNT was evaluated in mice before and after challenge. The total dose of toxin each pig received was 8.4 μg, or 50 mouse $LD_{50}$. Toxin was administered in three equal doses over a three day period beginning approximately two weeks following vaccination.

Results of the challenge were evaluated approximately 28 days following the first dose of toxin. The percent weight gain was calculated by the number of pounds gained in the 28 days following challenge divided by the weight, in pounds, at challenge. Nasal turbinate atrophy was evaluated by cross-section of the snout at the first premolar tooth as follows: score 0, normal; score 1, minimal atrophy; score 2, moderate atrophy; score 3, substantial atrophy; score 4, near complete atrophy; and score 5, complete atrophy.

Protocol I: Four gilts were vaccinated with a 2 ml dose of P. multocida free toxoid (A), described above in Example 4. Two gilts failed to farrow because of an infection of porcine parvovirus and were removed from the facility as soon as disease was evident. Pigs born of the two remaining gilts were vaccinated at 13 days of age (gilt 637, 7 pigs) and 9 days of age (gilt 638, 4 pigs) with a 2 ml dose of P. multocida free toxoid (B), described in Example 4. Second vaccinations were administered to all pigs two weeks later. Pigs were challenged with a dose of toxin two weeks following the second vaccination. Gilts from the same herd with farrowing dates similar to vaccinated gilts provided contemporary unvaccinated control pigs.

Following challenge, vaccinated and unvaccinated control pigs were commingled until they were slaughtered for final scoring. Table II illustrates the effects of challenge on pigs which were farrowed from dams vaccinated with two doses of vaccine A, and which were themselves vaccinated (VX) with two doses of free toxoid vaccine B, compared to unvaccinated (NonVX) animals. These results show significantly lower snout scores and significantly better weight gains in the vaccinated group.

TABLE II

| Group | No. | Weight at Challenge | Weight at Slaughter | Weight Gain (lb) | Weight Gain % | Mean Snout Score |
|---|---|---|---|---|---|---|
| VX | 10 | 26.20 | 39.60 | 13.40 | 54.27 | 1.00 |
| Non-VX | 8 | 22.88 | 31.56 | 8.69 | 35.30 | 2.34 |

Protocol II: Four gilts were vaccinated with a 2 ml dose of vaccine A. One gilt failed to farrow because of an infection of porcine parvovirus and was removed from the facility as soon as disease was evident. Pigs from remaining gilts were challenged with toxin as follows: 9 pigs from one gilt at 10 days old; 2 pigs from a second gilt at 12 days old; and 6 pigs from a third gilt at 4 days old. Gilts from the same herd with farrowing dates similar to vaccinated gilts provided contemporary unvaccinated control pigs.

Vaccinated and unvaccinated control pigs were challenged prior to weaning and thereafter commingled until slaughtered for final scoring. Table III summarizes the effects of challenge on pigs farrowed by dams which received two doses of vaccine A. The data are presented (a) independently of litter, and (b) by litter averages.

These results show significantly lower snout scores and significantly better weight gains in the vaccinated group. These observations indicate that two doses of vaccine A given to dams induced the production of antitoxin that was passively transferred to otherwise susceptible pigs. Furthermore, the duration of passive protection was at least 10 to 12 days.

TABLE III

| Group | No. | Weight at Challenge | Weight at Slaughter | Weight Gain (lb) | Weight Gain % | Mean Snout Score |
|---|---|---|---|---|---|---|
| (a) | | | | | | |
| VX | 15 | 6.87 | 21.00 | 14.13 | 205.83 | 3.02 |
| Non-VX | 5 | 8.20 | 16.40 | 8.20 | 100.00 | 3.70 |
| (b) | | | | | | |
| VX | | | | | | |
| Gilt 629 | 7 | 8.71 | 21.50 | 12.79 | 147.09 | 3.68 |
| Gilt 639 | 2 | 8.00 | 29.25 | 21.25 | 268.65 | 2.38 |
| Gilt 633 | 6 | 4.33 | 17.67 | 13.33 | 310.28 | 2.46 |
| Gilt Avg | | 7.02 | 22.81 | 15.79 | 242.01 | 2.84 |
| Non-VX | 5 | 8.20 | 16.40 | 8.20 | 100.00 | 3.70 |

EXAMPLE 6

ELISA TO QUANTIFY ANTIBODY

Pig sera and colestrum samples from the experiments of Example 5 were tasted for antibodies against the toxin by a kinetic EISA. Briefly, purified toxin (250 ng/well) in 0.1M sodium borate, pH 9.1, was adsorbed to flat-bottom 96 well Nunc microtiter plates overnight at 4° C. Plates were then blocked at 37° C. for 30 minutes with 10% nonfat dried milk in PBS with 0.05% Tween-20 (blocking buffer). Blocking buffer was rinsed from the plates with two PBS/0.05% Tween-20 (PBS/Tween) rinses, followed by a PBS rinse. Sera were diluted 1:100 in blocking buffer, and 50 μl samples were added to each of four wells. Plates were incubated for 60 minutes at 37° C., and then rinsed as above.

Goat-anti swine IgG (heavy and light chain specific)-horseradish peroxidase [Kirkegaard and Perry Laboratories, Gaithersburg, Md.] was diluted 1:500 in blocking buffer, and added (50 μl) to each well. Following a 60 minute incubation at 37° C., plates were rinsed as above. ABTS substrate (2,2'-axino-di-3-ethyl-benzthiazoline sulfonate) [Kirkegaard and Perry] was added, and plates were read immediately on a Vmax ELISA reader at 405 nm [Molecular Devices Corporation, Palo Alto, Calif.]. Each well was read eight times during a one-minute interval, and the rate of the enzymatic reaction was calculated.

Rates were calculated as the change in milli units of optical density (mOD) per minute. Thus a reading of 100 mOD per minute would be equal to an OD of 1.0 in 10 minutes. Values were then corrected for the amount of serum used per well and reported as mOD/min/ml of serum. For instance, if 50 μl of serum produced a reading of 100 mOD per minute, the reported value would be 2,000 mOD units per minute per ml.

The following controls were included on each ELISA plate. (1) Serum control: each diluted pig serum was placed in a well that did not contain antigen, then exposed to all subsequent reagents to check for non-specific adsorption to the plate. At the dilution of pig sera (1:100) used, no color greater than that obtained in the negative serum control was seen. (2) Negative pig serum control: each plate included three wells of a known negative pig serum diluted 1:100 in blocking buffer. (3) Positive pig serum controls: serum containing specific antibodies to the toxin was diluted in negative pig serum to obtain sera containing high, moderate, and low concentrations of specific antibody. These three sera were diluted 1:100 in blocking buffer and placed in triplicate on each plate. Background, or non-specific reactivity, was determined in wells that contained all reagents except pig serum.

Table IV below summarizes the ELISA titers of the dams and pigs vaccinated with toxoid vaccines A and B, respectively, according to Protocol II (Example 6). The table gives the geometric mean titers of sera taken before the first and second dam vaccinations, of the colostrum, and of sera taken before the first and second pig vaccinations, challenge, and slaughter, as compared to unvaccinated controls (Non-Vx).

TABLE IV

| | Geometric Mean ELISA Titers | | | | | | |
|---|---|---|---|---|---|---|---|
| Group | 1st Dam Vx | 2nd Dam Vx | Colostrum | 1st Pig Vx | 2nd Pig Vx | Challenge | Slaughter |
| VX | 21.71 | 0 | 173.00 | 0.99 | 1.73 | 109.03 | 139.07 |
| Non VX | 25.35 | 12.34 | 83.38 | 1.45 | 1.72 | .38 | 8.64 |

These results indicate that two doses of vaccine A given to dams, followed by two doses of vaccine B given to their pigs, induced immunity to the toxin in otherwise susceptible pigs.

From the same study (Protocol II, Example 6) Table V summarizes the ELISA titers of vaccinated (vaccine A) and unvaccinated dams and their unvaccinated pigs.

TABLE V

| | Geometric Mean ELISA Titers | | | | |
|---|---|---|---|---|---|
| A: Group | 1st Dam Vx | 2nd Dam Vx | Colostrum | Challenge | Slaughter |
| Vx | 28.19 | .76 | 104.31 | 7.98 | 22.53 |
| Non-Vx | 27.56 | 15.53 | 80.60 | .19 | .75 |

| Individual ELISA titers | | | | | |
|---|---|---|---|---|---|
| | 1st Dam | 2nd Dam | Geometric mean titers of litters at: | | |
| B: Group | Vx | Vx | Colostrum | Challenge | Slaughter |
| Vaccinated | | | | | |
| Gilt 629 | 21.80 | 5.80 | 70.60 | 1.66 | 29.15 |
| Gilt 639 | 29.20 | — | 18.60 | 26.07 | 25.39 |
| Gilt 633 | 35.20 | — | 154.10 | 36.43 | 16.03 |
| Average | 27.73 | 1.93 | 81.10 | 21.39 | 23.03 |
| Unvaccinated | | | | | |
| Gilt 636 | 23.40 | 10.80 | 66.80 | — | 12.40 |
| Gilt 631 | 30.60 | 11.90 | 135.90 | — | 0.20 |
| Gilt 626 | 19.80 | 17.60 | 76.70 | — | 9.40 |
| Gilt 635 | 40.60 | 20.40 | — | — | — |
| Gilt 632 | 27.60 | 19.60 | 60.60 | 4.60 | — |
| Average | 28.40 | 16.06 | 68.00 | 0.92 | 4.4 |

Table VI shows a summary of challenge-of-immunity studies for dam and pigs vaccinated with various doses (in relative toxoid units, RU) of free toxoid preparations.

TABLE VI

| RU Administered to: | | | Significant | Protection against |
|---|---|---|---|---|
| Dams | Pigs | No. | Weight Loss | Turbinate atrophy |
| 876 ± 32 | 307 ± 70 | 10 | Yes | Yes |
| 876 ± 32 | 0 | 15 | Yes | Yes |
| 391 ± 52 | 0 | 10 | No | No |
| 0 | 391 ± 52 | 9 | No | No |

The data shows significant protection of pigs farrowed by dams vaccinated with two doses of a vaccine containing 876±32 RU of free toxoid. In pigs or pregnant gilts, two doses of experimental lots containing between 300 and 400 RU/dose, did not appear to induce protection.

EXAMPLE 7

PREPARING *E. RHUSIOPATHIAE* VACCINE COMPONENT

*Erysipelothrix rhusipathiae* is prepared for use in a vaccine composition, either alone or, preferably, in combination with the *P. multocida* components described above. Preferably, the *E. rhusiopathiae* component is derived from serotype 2, which is the most prolific yielder of immunogen which is common to all *E. rhusiopathiae* serotypes [R. L. Wood, *J. Amer. Vet. Med. Assoc.*, 184: 944–948 (1984)]. Currently, the preferred strain is CN3342 [Smithkline Beecham].

A. Cell Culture

The following culture medium is free of crude organic matter, such as serum and ox bile, two ingredients traditionally used in erysipelothrix cultures. This has the effect of decreasing the frequency and severity of adverse reactions. The step of centrifuging to remove the bacterial cells also aids in decreasing the number and strength of adverse reactions, the common immunogen being in the supernatant fluid.

*E. rhusiophathiae* is cultured in seed medium made up of 2.0–3.0% protease peptone [Difco or equivalent], 0.25–0.75% yeast extract [Difco or equivalent], 0.1–0.3% Tween-80 [polyoxyethylene-srobitan monooleate], 1.0–2.0% $K_2HP_4$, in deionized water. The pH is adjusted to approximately 7.0±0.2 with 10N NaOH. The medium is sterilized by autoclaving at 121° C. for 30 minutes. After autoclaving, sterile 50% dextrose solution is added to a final concentration of 1.0–2.0% w/v.

One of skill in the art could make modifications to the ingredients of, and the amount of each used in, the above culture medium. For example, in the above medium protein digests other than protease peptone may be used; Tween 80 may be replaced by other soluble compounds of oleic acid, e.g. Tween 85; or, additional growth factors may supplement or be substituted for yeast extract, e.g. marmite.

An ampule of working seed is thawed and its contents tranferred to a container of seed medium. The seed culture is incubated at 37° C. for 12 to 24 hours, with agitation. If microscopic examination of a Gram-stained slide indicates a satisfactory culture, the culture is used to inoculate the production culture. Alternatively, it may be used to inoculate a second seed culture which is then used to inoculate the production culture. Inocula are 2 to 10% of the culture volume.

Production cultures are incubated at 30°–39° C., with agitation, for an average of 5 to 8 hours. Sterile 10N sodium hydroxide solution is added to the cultures through the incubation period to maintain a pH of 7.0–7.6. Sterile 50% dextrose solution may be added as needed. When the maximum OD is attained (stationary phase), the inactivating agent is added to the culture as described below. Alternatively, inactivation may be performed earlier, during the exponential phase or transitional phase of growth.

B. Inactivation of Bacteria

Inactivation is performed as follows. A sample of the *E. rhusiopathiae* is taken from the culture and Gram stained. If this reveals a pure culture, a sufficient amount of formaldehyde solution is added to give a final concentration of 0.5% by volume. The culture is transferred to a sterile tank and placed in a 37° C. incubator for 24 hours under constant stirring. (The formaldehyde concentration may be decreased or increased; however, the incubation time must be adjusted to compensate.) Inactivation is determined by a bulk sterility test in accordance with 9 CFR §113.26. The product is stored at 4°–10° C. until ready for further processing.

C. Vaccinal Fluid Preparation

Following inactivation, the culture is cooled and transferred aseptically into a holding vessel. The culture is then aseptically clarified by passage through a continuous flow centrifuge. After clarification, the fluid fraction is concentrated by ultrafiltration to a calculated OD of 16.67. The result is a sterile immunogenic fluid.

This degree of concentration, i.e., that obtained by concentration to an OD of 16.67, permits (after the addition of aluminum hydroxide gel to a final concentration of 25%) 0.3 mL of the mixture to contain the antigenic dose of 3.75 opacity units (1 opacity unit is contained in 1 mL of OD 1). This 0.3 mL is the volume of *E. rhusiopathiae* used in a combination vaccine having a total dose of 2 mL.

EXAMPLE 8

PREPARING *B. BRONCHISEPTICA* VACCINE COMPONENT

*Bordetella bronchiseptica* is prepared for use in a vaccine composition, either alone or, preferably, in combination with the *P. multocida* toxoids and, optionally with other active ingredients described herein. Preferably, the *B. bronchiseptica* seed is derived from swine with atrophic rhinitis. Currently, the preferred strain is strain 2–9 NADC [National Animal Disease Center, Ames, Iowa] However, strain J4 [SmithKline Beecham] may also be used.

A. Cell Culture and Production

The culture medium used for propagation of *Bordetella bronchiseptica* is a modified Stainer-Scholte defined synthetic minimal medium. The following procedure is used to prepare 1 liter of defined synthetic salt medium 2.4 g L-praline, 0.67 g L-glutamic acid, 2.5 g NsCl, 0.5 g $KH_2PO_4$, 0.2 g KCl. 6.075 Trizma base [Sigma #T 1503]. These ingredients are dissolved, in order with stirring, in 1000 mL of distilled or deionized water. The pH is adjusted to 7.0±0.2 units with HCl and the media is sterilized by autoclaving.

One hundred of each of three 10x stock solutions are prepared as follows. An L-cysteine solution is prepared by dissolving 0.4 g of L-cysteine 4 mL of 4N HCl and then bringing the volume of 100 mL with distilled or deionized water. A ferrous sulfate, calcium chloride, magnesium chloride solution is prepared by dissolving 0.125 g $FeSO_4·7H_2O$, 0.3 g $CaCl_2·2H_2O$, and 1.0 g $HgCl_2·6H_2O$ in 100 mL of distilled or deionized water. These ingredients are dissolved individually and in order, with stirring before addition of the next ingredient. An ascorbic acid, nicotinamide, sodium acetate solution is prepared by dissolving 0.2 g ascorbic acid, 0.10 g nicotinamide, and 2.0 g sodium acetate per 100 mL of distilled or deionized water.

These three solutions are then filter sterilized and the L-cysteine and vitamin solutions are stored at 2° to 7° C. These stock solutions are added to the minimal salt solution described above in a volume of 10 mL per liter to form the culture medium.

Between 1 to 5% of a suspension of reconstituted, lyophilized master seed or thawed working seed is inoculated into a flask containing the above described culture medium. The culture is incubated at 36° C.±1° C. for 16 to 30 hours with aeration. Following satisfactory growth, this culture medium is transferred into a seeding flask containing fresh medium using 1 to 5% inoculum. This second subculture is incubated as before. Production cultures are inoculated with the second actively growing subculture using 1 to 5% inoculum.

Production cultures of *B. bronchiseptica* are grown in fermentors. The culture is incubated at 36° C.±1° C. for 16 to 40 hours following inoculation. The setpoint for dissolved oxygen is positioned at 80% of a calibrated maximum (saturation). Preferably, the setpoint for dissolved oxygen may be positioned at 40%. This permits faster and, thus, a shorter incubation period of between about 6 and 16 hours.

Dissolved oxygen content is maintained by aeration With sterile air and by agitation. Sterile antifoam solution is added before the media is inoculated. The pH of the culture is maintained at 7.2–7.4 by the addition of propionic acid.

B. Fluid Inactivation and Preparation

As described below, either beta-propiolactone (BPL) or formaldehyde may be used for the inactivation of the culture. When BPL is used, it is added to the culture at the end of the growth period. A second addition of BPL is made 2 to 18 hours later. The final concentration of BPL should not exceed 1:500 (0.2%). The culture is incubated at less than 20° C. with constant agitation for at least 12 hours. Alternatively, at end of the growth period, formalin (Formaldehyde Solution USP) is added to the culture at a final concentration of 0.4% of the total volume. The culture is incubated at 35° to 37° C., with constant agitation for at least 24 hours.

Following inactivation, a representative sample is taken and tested for completion of inactivation by direct plate count on trypticase soy agar plates using 0.5 mL inoculum for each of 3 plates. Bulk samples are tested for sterility in thioglycolate at 37° C. and soy broth at 22° C. The inactivated culture may be transferred into sterile storage vessels and stored at 2° C. to 7° C. until assembled.

Sterile aluminum hydroxide gel (equivalent to 2% $Al_2O_3$) is added to the inactivated culture at a concentration of 5% volume/volume, to control free endotoxin. An adsorbed whole culture results.

C. Alternative Method of Fluid Preparation

In one preferred alternative method, rather than inactivating the culture with BPL, the culture may be prepared for use in a vaccine by the glutaraldehyde method described in Brown et al, U.S. Pat. No. 4,888,169. This method involves inactivating the culture by the addition of glutaraldehyde to the culture medium. In order to completely inactivate the *B. bronchiseptica* exotoxin, the method described in U.S. Pat. No. 4,888,169 is adjusted by increasing the glutaraldehyde concentration to between 0.2 and 0.25% v/v and incubating at 37° C. for about 24 hours.

The glutaraldehye acts to bind the endotoxin and obviates the need for adsorbing the culture with aluminum hydroxide as described above.

D. Standardization of Antigen Concentration

B. Bronchiseptica is standardized to contain not less than 1500 nephelometric units per dose when inactivated with BPL; not less than 3000 nephelometric units when inactivated by the glutaraldehyde method, and not less than 4000 nephelometric units per dose when inactivated with formaldehyde. The nephelometric units are based on the value measured at the time of harvest.

When this component is used in a vaccine composition (having a 2 mL dose) containing several other antigenic components, it makes up approximately 0.2 to 1.0 mL of the 2 mL vaccine dose.

EXAMPLE 9

A COMBINATION VACCINE

Combination vaccines may contain the cell-bound toxoid of Example 1 or 2, and/or the soluble toxoid of Example 3 with optional components, such as other inactivated microorganisms, e.g. B. bronchiseptica, other strains of P. multocida, and M. hyopneumoniae.

One exemplary efficacious vaccine composition contains free toxoid and cell-bound toxoid of P. multocida type D, described above, with the B. bronchiseptica component described in Example 8.

One exemplary formulation for a combination vaccine consists of the following components:

| Component | Vol/dose (ml) | Vol (ml) |
|---|---|---|
| P. m. cell-bound toxoid | 0.200 | 25.00 |
| Free toxoid (650 U/ml) | 0.242 | 30.25 |
| B. bronchiseptica | 0.300 | 37.50 |
| oil/lethicin | 0.100 | 12.50 |
| Tween 80 | 0.056 | 7.00 |
| Span 80 | 0.024 | 3.00 |
| Saline | 1.078 | 134.75 |
| TOTALS | 2.000 | 250.00 |

For emulsification, these components were combined and emulsified, as a single batch, for 2 minutes. For production scale, it is anticipated that metered in-line rather than batch combination is desirable.

Other ingredients may be added to, or may replace existing ingredients in, the specific formulation above. In addition to the oil/lecithin, the aluminum hydroxide gel to which the cell-bound toxoid is adsorbed also serves as an adjuvant. One or more complete or partial bulk lots of each fraction are combined with adjuvant and saline diluent to obtain the standard antigen concentration.

EXAMPLE 10

M. HYOPNEUMONIAE VACCINE COMPONENT

A Mycoplasma hyopneumoniae vaccine component is useful in a combination vaccine of the invention for preventing mycoplasmal pneumoniae in swine. Currently, a desirable immunogenic amount of inactivated organism is approximately $10^9$ color changing units (CCU). However, it is anticipated that under optimal conditions this dose amount may be reduced to between about $5 \times 10^8$ and $5 \times 10^9$ CCU. Usually, approximately 0.1 to about 0.3 mL is required to obtain the required dose amount.

Typically, in preparing a combination vaccine containing a M. hyopneumoniae component, this culture is simply added to the liquid bulk vaccine formulation.

A. Propagation and Culture of M. hyopneumoniae

M. hyopneumoniae strain P-5722-3 was furnished courtesy of Dr. Charles Armstrong, Purdue University, and deposited with the American Type Culture Collection under Accession No. 55052. This strain has the immunochemical and biochemical characteristics of being mannose positive, arginine negative, and urease negative. The strain is positive for growth inhibition with anti-M. hyopneumoniae antiserum and positive by direct fluorescent antibody test with anti-hyopneumoniae fluorescein-conjugated antibody. This strain was propagated as described below.

A culture medium was prepared according to the following procedure. An 83% PPLO broth, without crystal violet [Difco Laboratories, Detroit, Mich.] was conditioned by treating the broth with an anion exchange resin [Amberlite, Sigma IRA400-chloride form] for one to four hours, at the rate of 500 grams of resin for every ten liters of broth.

Yeast extract was prepared by adding five hundred grams of active yeast granules to three liters of deionized water, stirred at room temperature. After thorough mixing, the suspension was stirred for an additional 15–45 minutes after which 16.2 ml of 10N NaOH was added, dropwise. The slurry was then autoclaved for 15–45 minutes at 121° C. The supernatant was decanted into a container and clarified by either centrifugation or microfiltration. To the clarified supernatant, 1N HCl was added at a rate of 2 ml per 100 ml extract. The extract was stirred for at least fifteen minutes at room temperature and then clarified as described above. The clarified extract was sterilized by autoclaving as described above or by microfiltration.

To the pretreated broth the following media components were added: 0.01% thallium acetate; 0.005% ampicillin; 0.0125% cysteine hydrochloride; 6.25% yeast extract, 1% dextrose; 10% swine serum (Gibco) heat inactivated; and, optionally, 0.0026% phenol red. The pH of the culture medium was adjusted to pH 7.5±0.2 and filter sterilized.

To initiate a production serial, frozen M. hyopneumoniae master seed was thawed and a 5–20% suspension inoculated into 100–3000 ml of the culture medium described above. The culture was incubated at 30° C. to 39° C. for 36 to 168 hours. Following satisfactory growth, the culture was transferred into a seeding container with fresh medium, using a 5–20% inoculum. This culture was incubated at 37° C.±1° C. for 36 to 96 hours.

Production cultures of M. hyopneumoniae are grown in fermentors, incubated at 37° C.±1° C. for 36 to 96 hours following inoculation. The dissolved oxygen content of the culture is maintained at between 20–40% by aeration with sterile air and agitation. Sterile antifoam may be used to control foam.

At the end of the growth period, the pH of the culture was raised to 7.6±0.2 and the pH maintained in this range for about one hour. To inactivate the organism, a filter-sterilized aqueous solution of 2-bromoethylaminehydrobromide (BEA) was added to a final concentration of approximately 4.0 mM. BEA is converted to the inactivating agent binary ethyleneimine (BEI) at the increased pH of the culture. The culture was incubated at 37° C.±1° C. with constant agitation for at least 24 hours.

After the 24 hour incubation, a filter sterilized aqueous solution of sodium thiosulfate, a standard neutralizing agent, was added to a final concentration of approximately 4 mM to neutralize excess BEI. The culture was incubated for an additional 24 hours at 37° C.±1° C. to complete inactivation.

B. Preparation of a Vaccine

Following inactivation of the vaccine component of the preceding example, a vaccine was formulated by adding the inactivated M. hyopneumoniae to the P. multocida cell-bound toxoid and/or other vaccine components of the invention. Sufficient inactivated M. hyopneumoniae was combined with the bulk liquid vaccine lot to obtain a minimum antigen concentration of approximately $10^9$ CCU per 2 ml dose.

Sterile 10% merthiolate and 10% ethylenediamine tetraacetic acid (EDTA, disodium or tetrasodium salt) solutions were added as preservatives. Sterile mineral oil [Drakeol] containing 5% to 40% by weight of lecithin (Central Soya) is emulsified in phosphate buffered saline and added to the bulk vaccine fluids to a final concentration of 5% v/v. This oil/lecithin combination serves as an adjuvant. The final concentration of between 0.7% to 3.2% Tween 80 and 0.3% to 1.8% Span was added as an emulsifier. Selected parabens (methyl p-hydroxylbenzoate, propyl p-hydroxylbenzoate, butyl p-hydroxylbenzoate) may be added as additional preservatives for the oil and emulsifiers.

EXAMPLE 11

VACCINE TESTS IN ANIMALS—SYNERGY BETWEEN SOLUBLE AND CELL-BOUND TOXOIDS OF P. MULTOCIDA

During the vaccine tests, it was surprisingly observed in the evaluation of the antibody response in swine, that combining the P. multocida cell-bound toxoid and free toxoid had more than an additive effect on the induction of antitoxin, compared to use of the cell-bound toxoid alone or the free toxoid alone.

In one experiment, groups of pigs were vaccinated with a vaccine composition containing the P. multocida cell-bound toxoid (Example 2) and preserved cultures of B. bronchiseptica and E. rhusiopathiae, or with the free soluble P. multocida toxoid of Example 3 only, or with the combined vaccine containing cell-bound toxoid with soluble toxoid added. Table VII demonstrates antibody response to vaccination with free toxoid alone, with the vaccine containing cell-bound toxoid alone and with a combination between these two vaccine components. The ELISA titers indicate a synergistic effect of this combination vaccine. This combination vaccine composition is believed to induce the best immunity in swine.

The post vaccination sera were also assayed for neutralizing antitoxin, the actual-protective antibody, by the method of Roberts and Swearingin, Am. J. Vet. Res., 49: 2168 (1988). The antitoxin values show a strong synergy of the free and cell-bound toxoids (Table VII). (Aluminum hydroxide content is 12% v/v; AMPHIGEN™ adjuvant content is 5% v/v).

Table VIII demonstrates the results of another experiment wherein a vaccine containing whole cell inactivated cultures of P. multocida (PmD), soluble toxoid and B. bronchiseptica inactivated whole cells (Bb), was used in guinea pigs and serum antibody levels measured by the EBL tissue culture assay [J. M. Rutter et al, Veterinary Record, 114: 393–396 (1984)]. In this experiment the combination vaccine dosage unit is 2 ml/dose. In this experiment 600 RU free toxoid failed to induce an appreciable anti-toxin response. In contrast, 600 RU free toxoid combined with inactivated cultures of P. multocida (PmD) (cell-bound toxoid) induced an antitoxin response level of 128. This demonstration serves as yet another example of immunologic synergy for soluble toxoid and inactivated cultures of toxigenic P. multocida.

TABLE VII

| No. Pigs | Bound Toxoid (ml) | Free Toxoid (RU) | Adjuvant | Serum Antibody Levels PRE Vx | Serum Antibody Levels POST Vx | Neutralizing Antitoxin units/ml POST Vx |
|---|---|---|---|---|---|---|
| 8 | 0 ml | 200 | Al$_2$OH$_3$ | <10 | 13 | <1 |
| 8 | 0 ml | 200 | AMPHIGEN-Al$_2$OH$_3$ | <10 | 16 | <1 |
| 8 | 2 ml | 0 | Al$_2$OH$_3$ | <10 | 93 | 20 |
| 8 | 2 ml | 0 | AMPHIGEN-Al$_2$OH$_3$ | <10 | 46 | 20 |
| 8 | 2 ml | 120 | Al$_2$OH$_3$ | <10 | 252 | 40 |
| 8 | 2 ml | 120 | AMPHIGEN-Al$_2$OH$_3$ | <10 | 302 | 80 |

TABLE VIII

| Bound Toxoid | Free Toxoid (RU) | Dose Fraction | Adjuvant | Serum Antibody Levels PRE-Vx | Serum Antibody Levels POST-Vx |
|---|---|---|---|---|---|
| Bb + PmD | 600 | 1/25 | AMPHIGEN-Al$_2$OH$_3$ | <2 | 128 |
| Bb + PmD | 300 | 1/25 | AMPHIGEN-Al$_2$OH$_3$ | <2 | 4 |
| Bb + PmD | 0 | 1/25 | AMPHIGEN-Al$_2$OH$_3$ | <2 | <2 |
| Bb | 600 | 1/25 | AMPHIGEN-Al$_2$OH$_3$ | <2 | 4 |
| Bb | 300 | 1/25 | AMPHIGEN-Al$_2$OH$_3$ | <2 | <2 |

Numerous modifications and variations of the present invention are included in the above-identified specification and are expected to be obvious to one of skill in the art. For example, use of other appropriate inactivated pathogens, other than B. bronchiseptica, E. rhusiopathiae, or M. hyopneumoniae may be employed in the combined vaccines of this invention. Similarly, other conventional adjuvants and inactive vaccine components may be employed in the formulations and selected by one of skill in the art. The dosages and administration protocols for use of these vaccine compositions may also be adjusted by one of skill in the art based on the animal to be vaccinated, the disease for which protection is desired and other related factors. Such modifications and alterations to the compositions and processes of the present invention are believed to be encompassed in the scope of the claims appended hereto.

What is claimed is:

1. A vaccine composition comprising an immunogenic amount of a Pasteurella multocida bacterin, said bacterin comprising a cell-bound toxoid, an immunogenic amount of an alkaline-toxoided Pasteurella multocida cell-free toxin, and a carrier suitable for internal administration.

2. The vaccine composition of claim 1, further comprising an immunogenic amount of one or more additional antigens.

3. The vaccine composition of claim 2, wherein said additional antigens are selected from the group consisting of a Bordetella bronchiseptica bacterin, an Erysipelothrix rhusiopathiae bacterin, inactivated Mycoplasma hyopneumoniae, and Escherichia coli antigens.

4. The vaccine composition of claim 1, wherein said Pasteurella multocida bacterin is prepared from a toxigenic Type D strain.

5. The vaccine composition of claim 4, wherein said toxigenic Type D strain is *Pasteurella multocida* Type D strain 8.

6. The vaccine composition of claim 1, further comprising one or more adjuvants.

7. The vaccine composition of claim 6, wherein said adjuvants are selected from the group consisting of dispersed oils, mineral oil and lecithin emulsion, $Al_2OH_3$, muramyl dipeptide, saponins, and Quil A.

8. The vaccine composition of claim 6, wherein said adjuvants are dispersed oils and $Al_2OH_3$.

9. A method of vaccinating an animal against *Pasteurella multocida* comprising internally administering to said animal the vaccine composition of claim 1.

10. The method of claim 9 wherein said vaccine composition further comprises an immunogeneic amount of one or more additional antigens, said additional antigens selected from the group consisting of a *Bordetella bronchiseptica* bacterin, an *Erysipelothrix rhusiopathiae* bacterin, inactivated *Mycoplasma hyopneumoniae*, and *Escherichia coli* antigens.

11. The method of claim 9 wherein said vaccine composition further comprises one or more adjuvants.

12. The method of claim 11 wherein said adjuvants are selected from the group consisting of dispersed oils, mineral oil and lecithin emulsion, $Al_2OH_3$, muramyl dipeptide, saponins, and Quil A.

13. The method of claim 11 wherein said adjuvants are dispersed oils and $Al_2OH_3$.

14. A method of vaccinating an animal against *Pasteurella multocida* comprising the sequential steps of internally administering to said animal an immunogenic amount of a *Pasteurella multocida* bacterin, said bacterin comprising a cell-bound toxoid, and internally administering to said animal an immunogenic amount of an alkaline-toxoided *Pasteurella multocida* cell-free toxin.

* * * * *